United States Patent [19]

Upsher

[11] 4,337,761
[45] Jul. 6, 1982

[54] LARYNGOSCOPE

[76] Inventor: Michael S. Upsher, 2957 Adeline Dr., Burlingame, Calif. 94010

[21] Appl. No.: 98,271

[22] Filed: Nov. 28, 1979

[51] Int. Cl.³ .............................................. A61B 1/06
[52] U.S. Cl. ........................................ 128/11; 128/16
[58] Field of Search ................... 128/9, 10, 11, 12, 13, 128/14, 15, 16, 17, 18, 19, 20, 21, 22, 23

[56] References Cited

U.S. PATENT DOCUMENTS

| | | | |
|---|---|---|---|
| 2,070,820 | 2/1937 | Allyn | 128/11 |
| 2,630,114 | 3/1953 | Hart | 128/11 |
| 3,153,267 | 10/1964 | Rowland | 128/16 |
| 3,809,072 | 5/1974 | Ersek et al. | 128/23 |
| 3,841,317 | 10/1974 | Awais | 128/17 |
| 3,913,568 | 10/1975 | Carpenter | 128/11 |
| 3,986,854 | 10/1976 | Schrivo et al. | 128/11 |
| 4,226,228 | 10/1980 | Shin et al. | 128/20 |

Primary Examiner—Kyle L. Howell
Assistant Examiner—T. J. Wallen
Attorney, Agent, or Firm—Flehr, Hohbach, Test, Albritton & Herbert

[57] ABSTRACT

A laryngoscope having a curved blade provided with means on the blade for removably holding an endotracheal tube and for guiding such tube into the pharynx, larynx and trachea of a patient after the blade has been inserted into the throat and has elevated the epiglottis. The blade has a slot extending along one margin for direct viewing into the pharynx during initial insertion of the blade. The blade also has a light source and a fiber optic viewing member near its outer end to permit remote indirect viewing of the epiglottis and larynx when direct viewing is no longer possible due to curvature of the pharynx and the blade. The fiber optic viewing member can either be removably attached to the blade or permanently attached thereto. Also, the blade can be of a material which can be flexed so that the blade is adjustable in shape to accommodate different pharangeal configurations of various patients. Generally, the blade is tubular to provide the guide feature therefor; however, the blade can have an open bottom margin and a guide wire extending along the bottom margin for receiving and guiding the endotracheal tube into place as the blade is inserted into the throat. Several embodiments of the electrical connection between the blade and the battery in the handle of the laryngoscope are disclosed.

32 Claims, 26 Drawing Figures

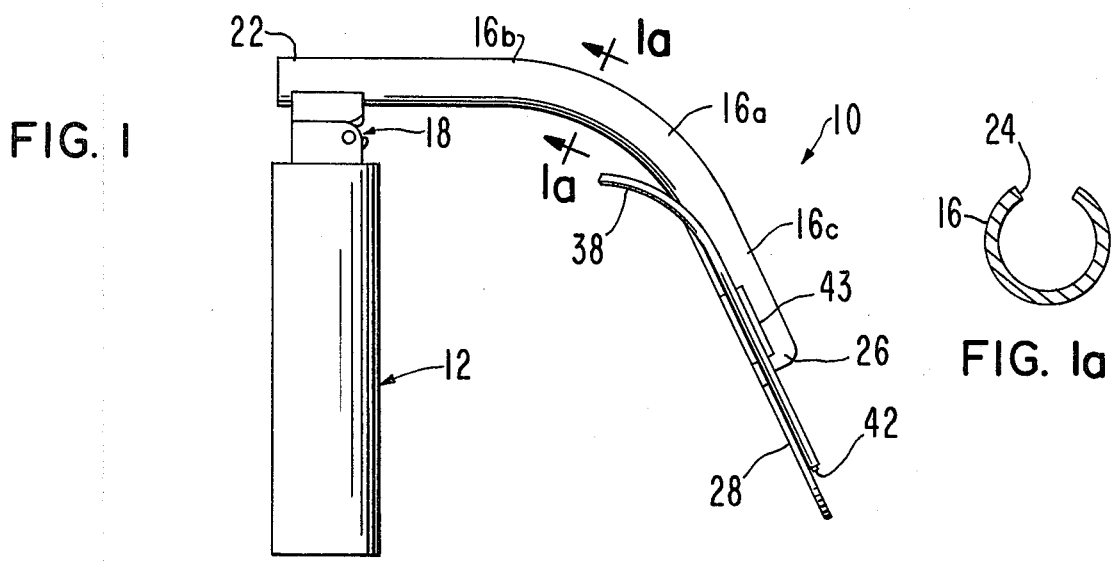
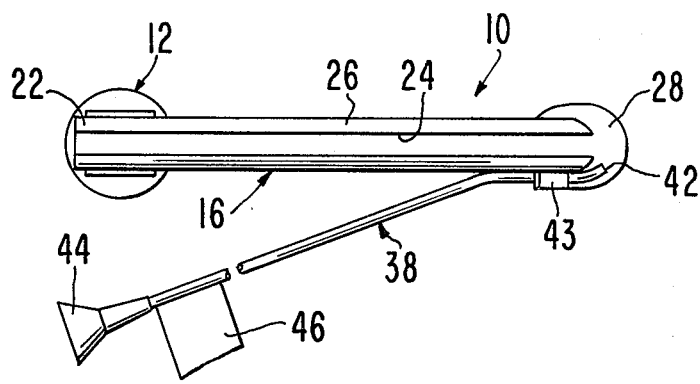
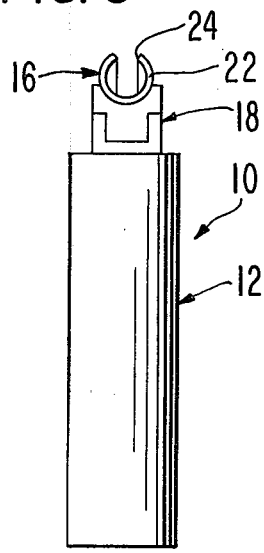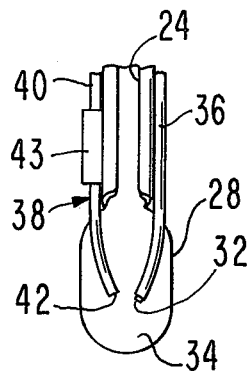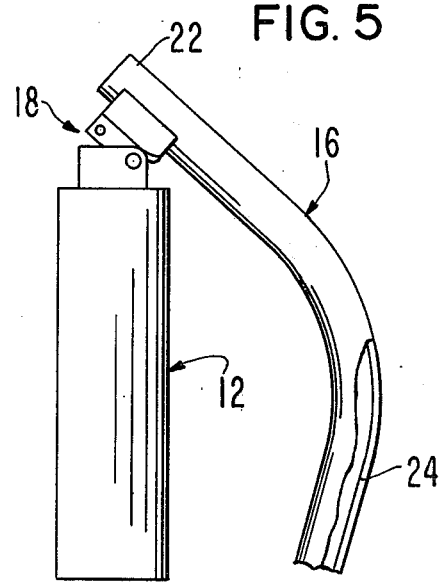

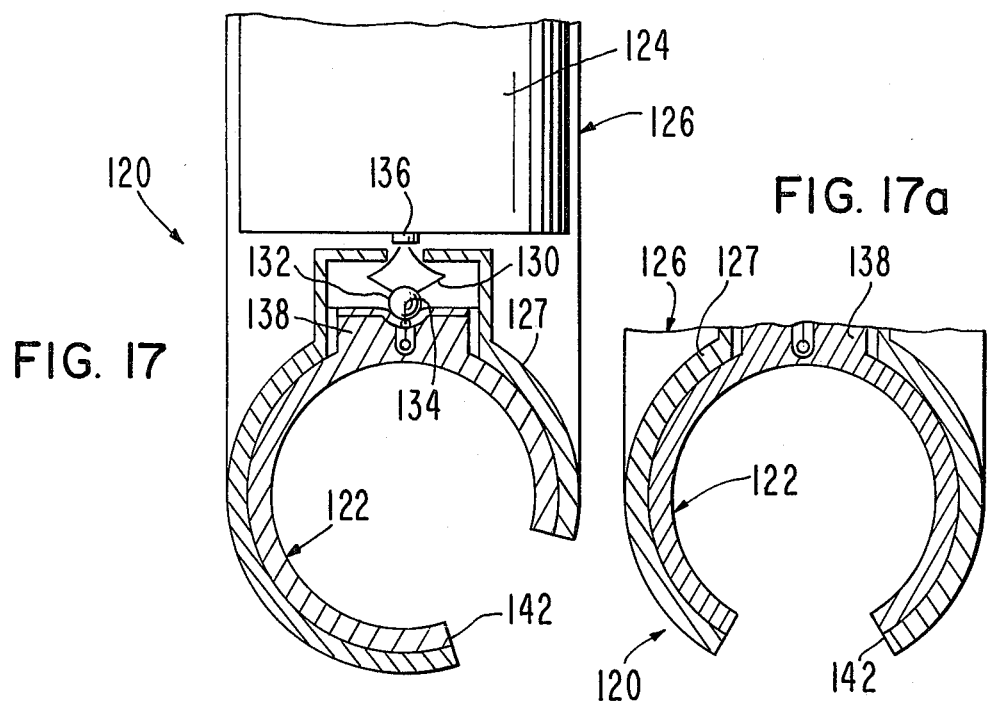
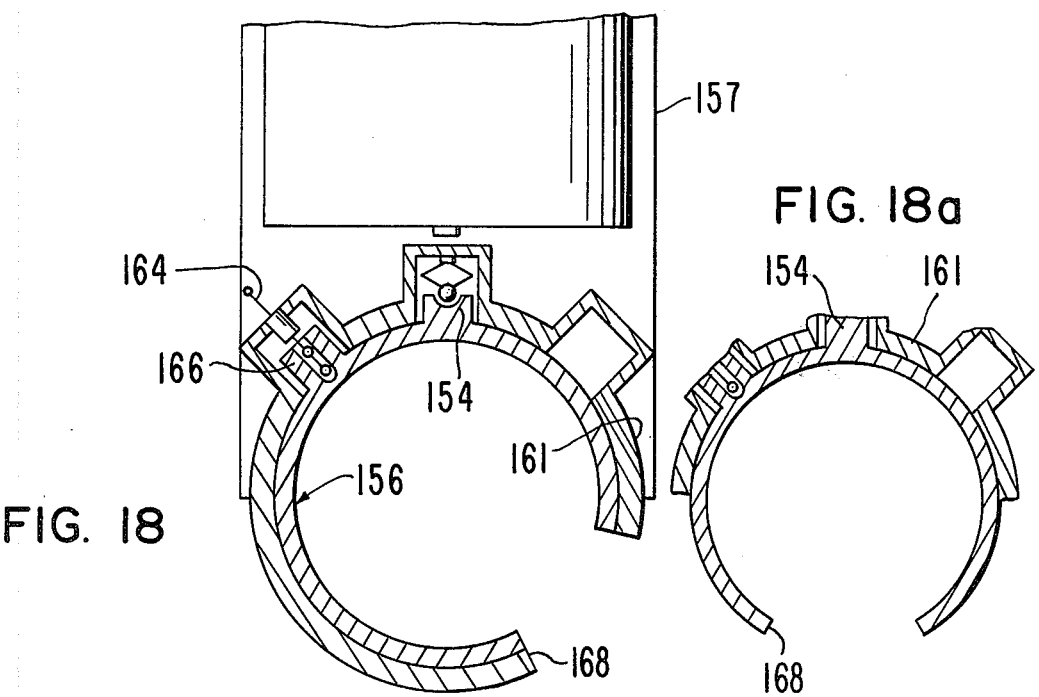

LARYNGOSCOPE

This invention relates to improvements in laryngoscopes and, more particularly to an improved laryngoscope which eliminates certain problems associated with insertion of conventional laryngoscopes into the pharynx, and the insertion of an endotracheal tube into the pharynx, larynx and trachea of a patient.

BACKGROUND OF THE INVENTION

In using conventional laryngoscopes, it is only by trial and error that the blade of the laryngoscope can be inserted into the pharynx in such a manner to elevate the epiglottis so that an endotracheal tube can be manually moved into the throat and into the larynx. This is because the larynx cannot always be directly and completely viewed during insertion of the blade. Usually, the laryngoscope is held in one hand as the endotracheal tube is held in the other hand because the laryngoscope has no means for both removably holding and guiding the endotracheal tube. This is an awkward situation because the user of the laryngoscope must be able to probe the pharynx without actually seeing the epiglottis in an attempt to elevate it yet the user must be ready to insert the tube as soon as the epiglottis is elevated. Most importantly, the line of sight from the eye of the anesthesiologist to the epiglottis and larynx must be straight using direct vision; whereas, the endotracheal tube must frequently be passed in a curved manner to conform with the normal anatomical pharyngeal curvature. The anesthesiologist, in these cases, is therefore asked to straighten out the normal physiological curve of the pharynx. This may result in damage to the patient's teeth, and "soft parts." Thus, considerable time and effort is expended in elevating the epiglottis and then inserting the tube, all of which must be done while causing only a minimum amount of discomfort to the patient.

The insertion of a conventional laryngoscope in the throat is a very tedious process in many cases and in some cases, injury is caused to the patient by virtue of the movements of the laryngoscope blade within the narrow confines of the physiological limitations of the patient. No satisfactory laryngoscope has been heretofore provided for effectively guiding the endotracheal tube into the throat while providing for the direct and indirect viewing of the throat during the insertion of the blade to elevate the epiglottis.

Representative laryngoscopes are disclosed in the following U.S. Pat. Nos. 2,646,036, 3,986,854 and 4,086,919. An endoscope which is related to a laryngoscope is disclosed in U.S. Pat. No. 3,896,793. The laryngoscopes of these references do not provide for the guiding of an endotracheal tube while permitting direct and indirect viewing of the throat during insertion of the blade of the laryngoscope. Moreover, there is no teaching or suggestion in these references that the blade can be shaped to fit different physiological throat configurations of various patients nor do the references suggest the need for improvements in laryngoscope blades.

Because of the shortcomings of conventional laryngoscopes as mentioned above, a need has arisen for improvements in laryngoscopes which facilitate the elevating of the epiglottis and the insertion of an endotracheal tube into the throat to minimize the discomfort to a patient.

SUMMARY OF THE INVENTION

The present invention satisfies the aforesaid need by providing an improved laryngoscope which eliminates the trial and error techniques used in the past with conventional laryngoscopes for elevating the epiglottis. To this end, the laryngoscope of the present invention has a blade provided with means for guiding an endotracheal tube into the larynx and trachea so that the insertion of the blade in the throat to elevate the epiglottis can be immediately followed by the passage of the tube through the tube-guiding part of the blade following which the blade can be removed, leaving the tube in place in the larynx and trachea. The blade has a slot on its back margin to permit direct viewing of the pharynx during initial insertion of the blade. For an intubating laryngoscope, this slot extends throughout the length of the blade and serves the additional purpose of allowing the removal of the laryngoscope from the pharynx while leavng the endotracheal tube in place. The slot is narrow enough to hold the tube in the blade but is wide enough to allow the tube to be separated from the blade when the tube yields so as to become elliptical in shape sufficiently to squeeze or pass through the slot. If the laryngoscope is of the operating type, the slot does not extend throughout the length of the blade but extends only a short distance from the outer end of the blade.

The blade has a light source at its outer end and a fiber optic viewing member near the light source to permit indirect viewing of the throat when direct viewing is no longer possible. Thus, the user can at all times be in visual contact with the larynx to minimize the time and effort required to elevate the epiglottis and insert the endotracheal tube.

The blade is preferably tubular to provide the guide feature therefor; however, the blade can be open and provided with a guide wire which receives the tube before the blade is inserted into the throat. The guide wire can be inserted in the lumen of the endotracheal tube or in a passage in the wall of the endotracheal tube. Thus, in the latter embodiment, once the blade is in the throat and has elevated the epiglottis, the endotracheal tube will be properly positioned in the pharynx so that the endotracheal tube can be advanced using the wire as a guide. The blade can then be backed-off, leaving the tube in the trachea, larynx and pharynx.

Other improvements of the laryngoscope of the present invention include the fact that the viewing slot, instead of being on the back margin of the blade, can be at any location within an arc 90° on each side of the back margin. This feature provides greater length of insertion of the blade before direct viewing is blocked due to the curvature of the blade. Also, the blade can be made of a suitable material which allows the blade to be normally rigid but capable of being flexed or shaped to fit the physiological throat configurations of different patients.

The primary object of this invention is to provide an improved laryngoscope which permits both direct and indirect viewing of the pharynx and larynx as the blade of the laryngoscope is inserted into the pharynx yet the blade has means for guiding an endotracheal tube in the place in the throat to thereby eliminate a trial and error method of elevating the epiglottis and guiding the endotracheal tube into position.

Another object of the present invention is to provide a laryngoscope of the type described which permits shaping of the blade to accommodate different throat configurations of various patients without distroying the capability of the blade to guide an endotracheal tube into the larynx past the epiglottis after the latter has been elevated by the blade.

Another object of the present invention is to provide a laryngoscope which can either be used for guiding an endotracheal tube or for guiding medical instruments into the laryngeal area and larynx. In either case, direct or indirect viewing of the throat can be achieved to permit immediate insertion of the blade of the laryngoscope into the throat without causing discomfort to the patient.

Other objects of this invention will become apparent as the following specification progresses, reference being had to the accompanying drawings for an illustration of various embodiments of the invention.

IN THE DRAWINGS

FIG. 1 is a side elevational view of a first embodiment of the laryngoscope of the present invention having a curved blade and fiber optic viewing device with its own self-contained light source;

FIG. 1a is an enlarged, cross-sectional view taken along line 1a—1a of FIG. 1;

FIG. 2 is a plan view of the laryngoscope of FIG. 1 showing the slot on the back margin of the blade;

FIG. 3 is a rear elevational view of the laryngoscope of FIGS. 1 and 2;

FIG. 4 is an enlarged, fragmentary, elevational view of the outer end of another embodiment of the laryngoscope showing a fiber optic viewing member of the type shown in FIGS. 1 and 2 but with an additional light source attached to the laryngoscope;

FIG. 5 is a view similar to FIG. 1 but showing the blade of the laryngoscope in a retracted condition;

FIG. 17 is an enlarged, fragmentary, cross-sectional view of a slotted blade of a laryngoscope showing an improved way of mechanically connecting the blade to the handle of the laryngoscope;

FIG. 17a is a view similar to FIG. 17 but showing the viewing slot of the blade at a different location;

FIG. 18 is a view similar to FIG. 17 but showing another way of coupling the blade of a laryngoscope to the handle thereof; and FIG. 18a is a view similar to FIG. 18 but showing the viewing slot thereof at a different location.

Figure 1B:
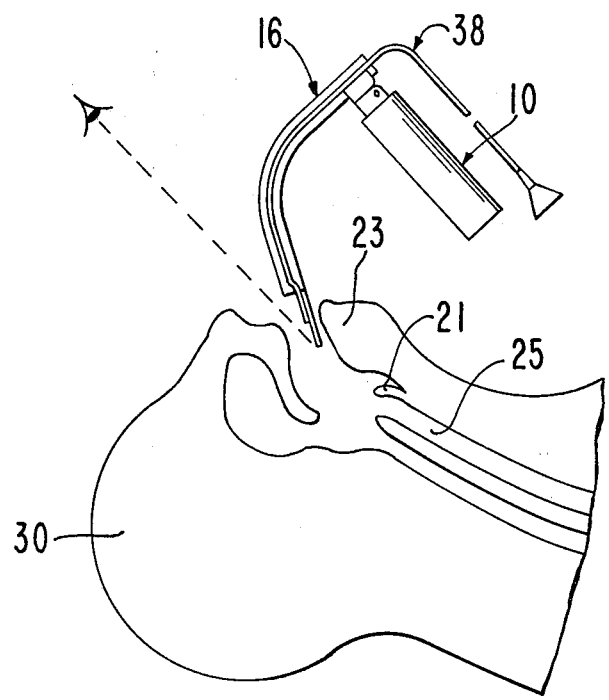
FIGS. 1b through 1e are schematic views of the laryngoscope as it is being sequentially inserted into the pharynx and larynx of a patient.

A first embodiment of the laryngoscope of the present invention is broadly denoted by the numeral 10 and is illustrated in FIGS. 1–5. Laryngoscope 10 includes a handle 12.

A tubular blade 16 is pivotally mounted by pivot means 18 to the normally uppermost end of handle 12. Pivot means 18 can be of any suitable construction and it allows the blade to be separated from the handle or to pivot from the operative position thereof shown in FIG. 1 to a collapsed or retracted position shown in FIG. 5. When blade 16 is removed from the handle or retracted, it can be readily stored or at least reduced in size for placement in a carrying case or the like. Pivot means 18 includes a detent 20 (FIG. 5) receivable in a recess (not shown) to releasably hold the blade in its operative position shown in FIG. 1, yet the detent allows the blade to be manually moved relative to handle 12 from the operative position of FIG. 1 to the retracted position of FIG. 5.

Figure 8:
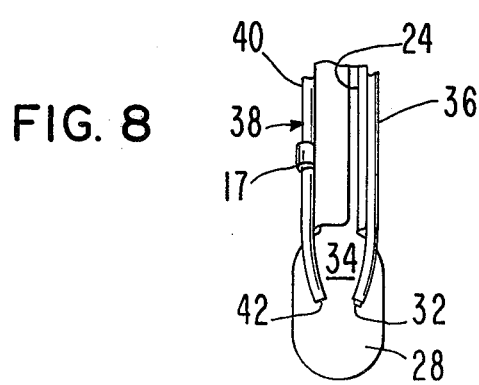
FIG. 8 is a view similar to FIG. 4 but showing the outer end of the laryngoscope of FIGS. 6 and 7 and the slot at one side of the back margin of the blade.
Figure 9:
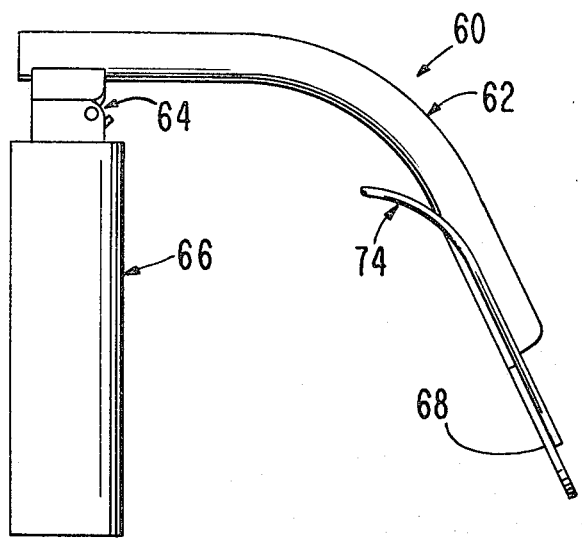
FIG. 9 is a view similar to FIGS. 1 and 6 but showing an operating laryngoscope forming a third embodiment of the present invention.

Blade 16 is transversely circular as shown in FIG. 1a throughout substantially its entire length. It can have other cross sections, if desired, so long as the blade is tubular. Its normally uppermost end 22 is open as shown in FIG. 3 and the blade has a slot 24 extending along an outer margin from end 22 to its outer, open, normally lowermost end 26. This margin will be considered the back margin of the blade with reference to the way it is used, such margin facing the user (FIGS. 1b through 1e) as the blade is inserted into the throat of a patient. While the slot is shown as being substantially on the back margin of tube 16, it can be at any location on either side of the back margin. Any such location can be within an arc of approximately 90° on either side of the back margin. FIG. 8 shows the slot to be on one side of the back margin.

Blade 16 has a central, curved part 16a (FIG. 1) and substantially straight end parts 16b and 16c. This shape is chosen because it meets the physiological throat shapes of most patients. Also, blade 16 has a flat pad or extension 28 rigid to end 26 and projecting outwardly and downwardly therefrom. Pad 28 has the outer peripheral shape as shown in FIG. 4 and is used to facilitate the insertion of the blade into the throat of a patient 30 in the manner shown in FIG. 1b. Pad 28 can have any one of a number of other shapes, if desired. The plane of pad 28 is substantially coextensive with the top margin of blade 16 adjacent to lowermost end 26.

A flexible fiber optic light source and viewing member 38 is provided to permit the user of laryngoscope 10 to illuminate and view the area of the throat of the patient. To this end, member 38 comprises a group of flexible optical fibers encased in a flexible sheath 40 with member 38 having an end face 42 providing a light source and a viewing plane adjacent to end face 34 of pad 28 as shown in FIG. 4. A tubular element 43 secured to the side of blade 16 near lowermost end 26 is provided to form a channel for removably receiving the lower part of member 38. The flexibility of member 38 permits it to be shifted about relative to blade 16 yet member 38 will be retained by element 43 so that end face 42 will remain in place near face 34 to permit illuminating and viewing of the throat area of the patient. The outer end of member 38 has an eyepiece 44 and a tubular handle 46 is coupled to sheath 40 near eyepiece 44, the length of member 38 being sufficient to permit eyepiece 44 to be over the eye of the user while blade 16 is manipulated during insertion of the blade into the throat of the patient. Handle 46 is provided with a battery for energizing the light source at face 42, such light source typically being an incandescent bulb. Sheath 40 has electrical conductors leading from the battery to the light source.

Member 38 can be a stock item purchased from a commercial supply house and is readily adapted for use with blade 16. Member 38 can be removed from element 43 and stored with laryngoscope 10 when the latter is in its retracted condition shown in FIG. 5.

An additional light source 32 can be used with member 38, if desired. To this end, light source 32 is carried by blade 16 near the upper flat surface 34 (FIG. 4) of pad 28 on the opposite side or the same side of face 34 as end face 42. The light source 32 can be caused to be energized immediately upon the movement of blade 16 into its operative position (FIG. 1) as is well known. Light source 32 can be of any suitable construction, such as a small incandescent bulb or it can be the end face of a fiber optics bundle which permits light to be projected therethrough from a light source at its opposite end. In any case, a sheath 36 is provided adjacent to blade 16. Sheath 36 either houses a pair of electrical leads or a group of optical fibers. Generally, light source 32 will be an incandescent bulb at the outer end of sheath 36 and the pair of leads in sheath 36 will be coupled to the bulb and to battery means within handle 12 when blade 16 is moved into its operative position.

Another possibility is to provide light source 32 when member 38 has no light source associated with it. Thus, there are a number of different combinations of light source and fiber optic viewing members in the present invention.

Blade 16 can be made from any suitable material that is generally rigid. For purposes of illustration, it is made of metal, but it could be made of plastic or other materials, if desired. The blade has a main purpose of guiding an endotracheal tube into the larynx of the patient after the user of the laryngoscope has elevated the epiglottis of the patient using pad 28 under direct and indirect viewing. Slot 24 is provided to permit direct viewing of the throat area when blade 16 is initially inserted into the mouth and moved at least through a limited distance toward the larynx of the patient. Eventually, the slot will not permit direct viewing because the curvature of the blade will block the view through the lower part of the slot. When this occurs, light reflected off the throat can be viewed through fiber optics member 38 when the eye of the user is adjacent to eyepiece 44 (FIG. 2). Thus, the blade can continue to be inserted into the throat even though direct viewing of the lowermost end 26 of the blade is impossible.

In use, patient 30 is generally in a supine position and the user of laryngoscope 10 is to the left of the patient's head when viewing FIGS. 1b through 1e with the eyes 49 of the user located as shown in FIG. 1b, to the left and above the head. The user is also in the vertical plane passing through the mid-line of the patient as he lies in the supine position. The eyes can then view along the sight line 48 into the throat area and, when holding handle 12 the part of the laryngoscope near pivot means 18, the user can commence the insertion of blade 16 and pad 28 into the mouth and the throat of the patient. The lower part of slot 24 allows for direct viewing along sight line 48 into the throat area as the blade is moved downwardly and toward the epiglottis 21 at the base of the tongue 23. The direct view of the epiglottis will usually be blocked before the epiglottis is elevated. However, at that time the throat and indirect viewing can be accomplished by use of the fiber optic member 38.

Figure 1C:
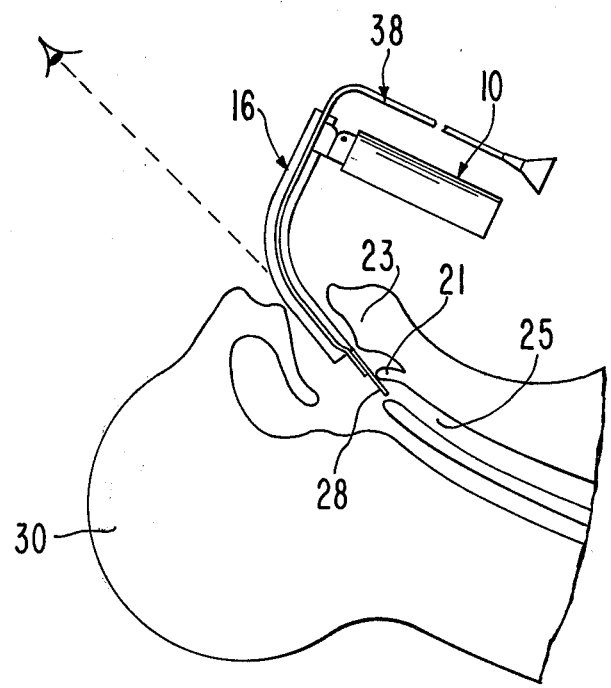
Figure 1D:
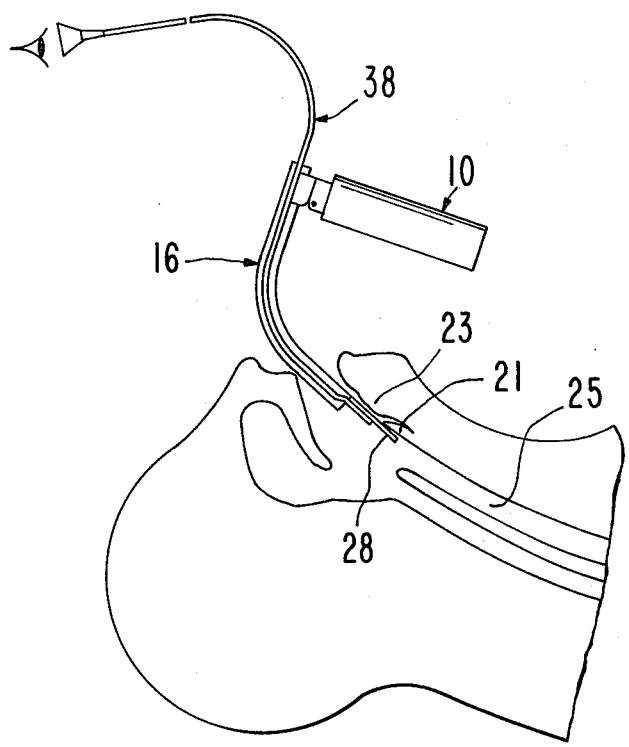
Figure 1E:
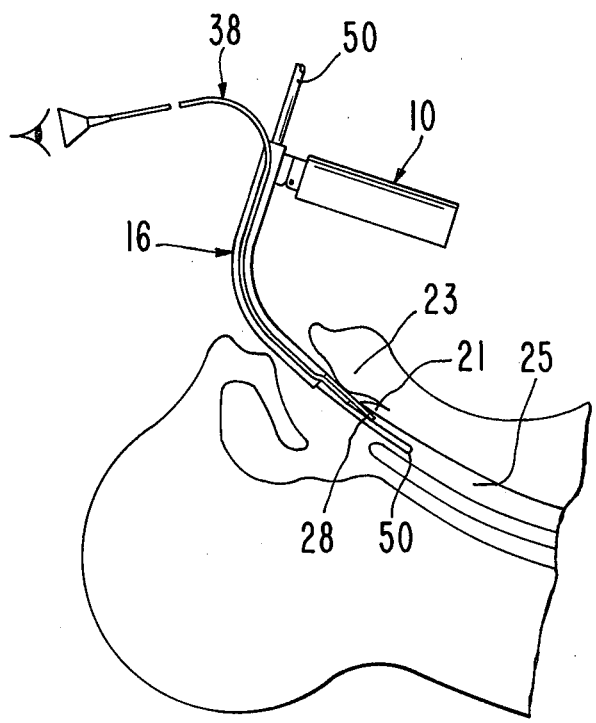

FIG. 1c shows the position of blade 16 after it has entered the mouth and as the pad 28 approaches the epiglottis 21. FIG. 1d shows the pad 28 as it elevates the epiglottis to open the trachea 25 and FIG. 1e shows the endotracheal tube 50 extending into the trachea 25.

The endotracheal tube is positioned proximally in the essentially straight portion of the blade 16b, in such a way that it does not obstruct the line of sight down the slot in the blade. The tube may be lubricated with a sterile lubricating jelly to facilate passage of the tube down the interior of the blade, under the epiglottis, and into the larynx and trachea after the blade has been placed in the proper position. Alternatively, when the blade is properly inserted, the endotracheal tube 50 can then be inserted by by hand into open end 22 and through blade 16 as the other hand continues to hold handle 12 or pivot means 18. When tube 50 is properly positioned, blade 16 can be moved longitudinally of tube 50 and out of the throat leaving the tube in place. The dimensions of the slot in the blade are such that the slot has a width less than the diameter of the endotracheal tube. Thus, the blade will removably hold the endotracheal tube within the blade, but the tube and blade can be separated by forcing or squeezing the endotracheal tube through the slot since the tube can yield to become elliptical in cross section so as to become narrowed sufficiently to pass through the slot. When the tube and blade are separated, the tube is left in the trachea. In this way, tube 50 can be quickly inserted and the user need not spend the time which has been previously required when using conventional laryngoscopes to insert tube 50 properly and comfortably in place.

Figure 6:
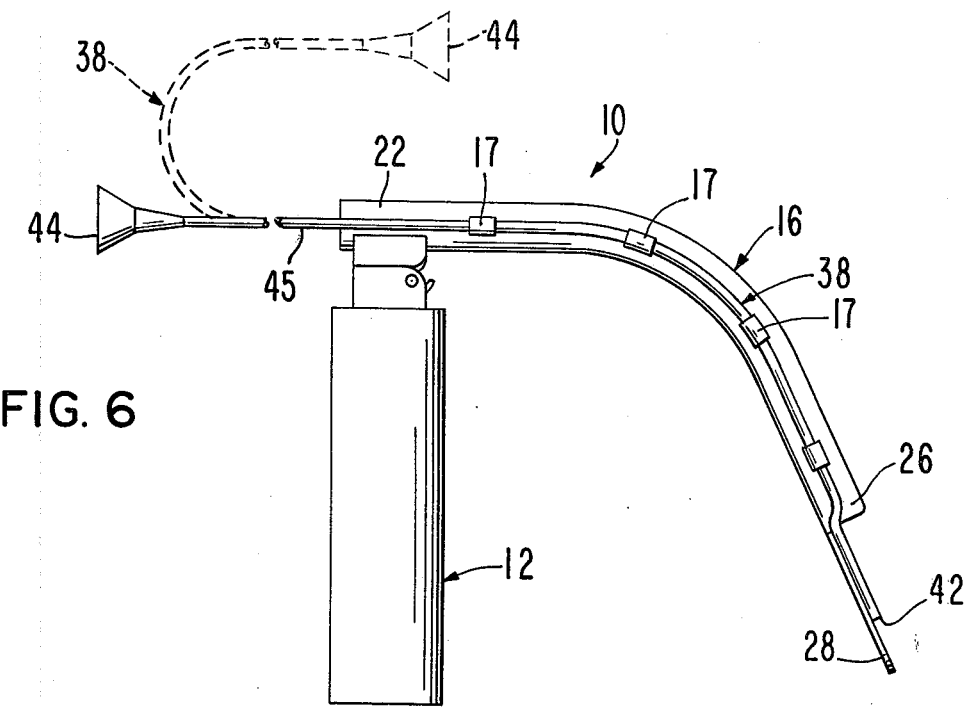
FIG. 6 is a view similar to FIG. 1 but showing a second embodiment of the laryngoscope of the present invention using a separate light source with the fiber optic viewing device.
Figure 7:
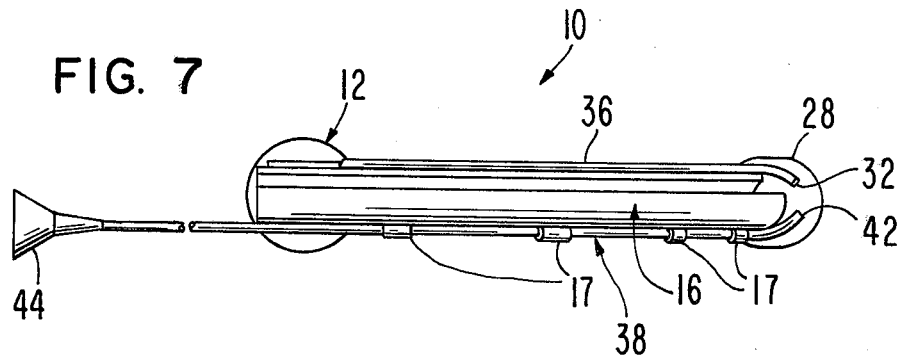
FIG. 7 is a plan view of the laryngoscope of FIG. 6.

While fiber optic member 38 is shown in FIGS. 1 and 2 as being removably mounted on the side of blade 16, member 38 can be permanently or rigidly secured to one side of blade 16 in the manner shown in FIGS. 6-8. To this end, member 38 will be of a construction and length sufficient to permit it to extend along one side of the blade from end 26 to end 22 thereof and to be rigidly secured to the blade in any suitable manner, such as by fasteners 17, by soldering or by an adhesive.

As an alternate way to connect member 38 to blade 16, the side of the blade can have a groove receiving the adjacent portions of member 38 and face 34 of pad 28 can have another groove for receiving end portion of member 38. The major diameters of the grooves are perpendicular to each other and will releasably hold member 38 in place without fasteners except for a hold-down screw near the end of the blade adjacent to the handle.

The outer end face 42 of the member 38 can still present a light source as well as a viewing plane if an electrical power source is included with member 38 such as a battery in a handle, such as handle 46. In the alternative, end face 42 can be adjacent to an additional light source 32 on pad 28 as described above with respect to FIG. 4 so that one or two light sources can be used, if desired.

Member 38, with eyepiece 44 at its upper end, will be flexible at least at location 45 thereof so that the member can move between the dashed and full line positions shown in FIG. 6 during insertion of the blade into the throat area of the patient. Thus, the portion of member 38 extending along a blade 16 can be rigid while the portion extending outwardly from end 22 of the blade can be flexible. As shown in FIGS. 7 and 8, slot 24 in blade 16 is slightly to the side of the back margin and may be at any other location within an arc of about 90° on either side of the back margin. It may be desirable to place the slot at this location to permit the insertion of a longer length of blade 16 before direct viewing along the slot is blocked. FIGS. 7 and 8 also show the additional light source 32 although such light source is optional if member 38 has a self-contained light source as described above.

Laryngoscope 10, with the modifications shown in FIGS. 6-8 is used in the same manner as that described above with respect to the laryngoscope of FIGS. 1-5. In any case, the endotracheal tube 50 is guided by blade 16 into the throat area once the blade is properly inserted into the throat after having elevated the epiglottis.

Figure 10:
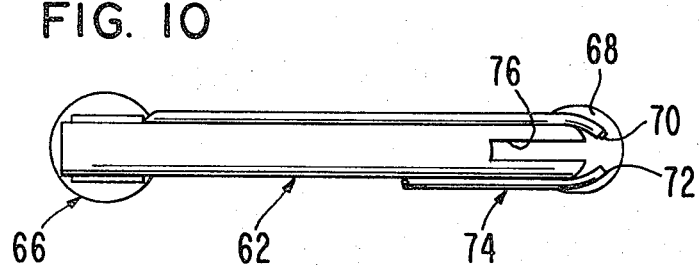
FIG. 10 is a plan view of the laryngoscope of FIG. 9.
Figure 11:
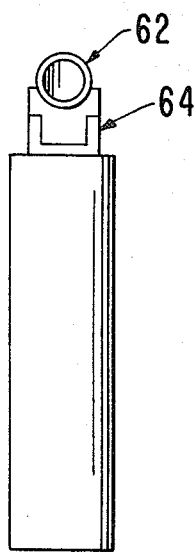
FIG. 11 is a rear elevational view of the laryngoscope of FIGS. 9 and 10.
Figure 12:
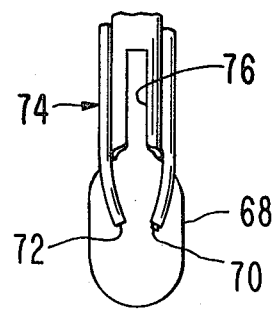
FIG. 12 is an enlarged, fragmentary, front elevational view of the laryngoscope of FIGS. 9 and 10 using a separate light source with the fiber optic viewing device.

The concepts of the present invention can be applied to an operating laryngoscope of the type shown in FIGS. 9-12. To this end, operating laryngoscope 60 has a tubular, generally rigid blade 62 pivotally coupled by pivot means 64 to one end of a handle 66 used for the same purpose as handle 12 of laryngoscope 10. Blade 62 is open at its opposed ends and has a pad 68 at its outer end adjacent to which a light source 70 and an end face 72 of a fiber optic viewing member 74 are positioned. As shown in FIGS. 10 and 12, blade 62 has a relatively short slot 76 near pad 68 while the remainder of the blade has no slot. Slot 76 permits direct viewing of the throat during initial insertion of the blade into the throat yet the solid or imperforate nature of the remainder of the blade permits surgical instruments to be guided toward and into the throat and larynx for operating purposes. Laryngoscope 60 is inserted into the throat in the same manner as described above with respect to laryngoscope 10. A light source can be self-contained in member 74, if desired.

Figure 13:
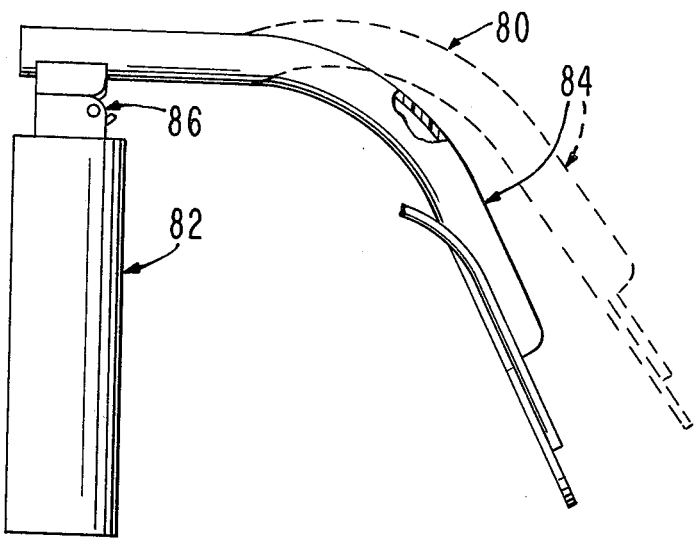
FIG. 13 is a view similar to FIGS. 1, 6 and 9 but showing a laryngoscope having a flexible blade to permit the changing of the shape of the blade.

FIG. 13 shows a laryngoscope 80 having a handle 82, a tubular, slotted blade 84 and pivot means 86 pivotally mounting one end of blade 84 on the upper end of handle 82. A fiber optic viewing member 87 can be provided with or without a self-contained light source. If with or without, additional light source, such as light source 32 in FIG. 4, can be provided.

Laryngoscope 80 is essentially the same in construction as laryngoscope 10 of FIGS. 1-5 and FIGS. 6-9 except that blade 84 while normally being a relatively rigid blade, is flexible or bendable so that it can be made to assume any one of a number of different shapes or curvatures. Once it is bent into the desired shape, it is rigid enough to maintain this shape during the manipulations of the blade in the pharynx. These manipulations may be necessary for inserting an endotracheal tube into the larynx of a patient. The full and dashed line positions of blade 84 show two of such shapes. This permits the blade to be accommodated to the different physiological throat configurations of various patients and thereby facilitates the insertion of the blade into the throat areas of such patients.

A suitable material for blade 84 is a thermo-plastic material, such as polyethylene, having a wall thickness which causes the blade to be relatively rigid yet, even at room temperature, can be bent or otherwise shaped to any desired curvature or straight condition at various locations along its length. Other thermoplastic materials can be used in which, upon slight heating of blade 84, such as by putting it in hot water, the blade can be manually flexed or shaped at certain locations to cause it to be or to assume a certain configuration depending upon the anatomy of the patient in whose throat the blade is to be inserted. In all such bending or flexing of the blade, the blade continues to remain tubular so that the blade can be used at all times for guiding an endotracheal tube into the throat past the epiglottis after the epiglottis has been elevated by the blade.

Figure 14:
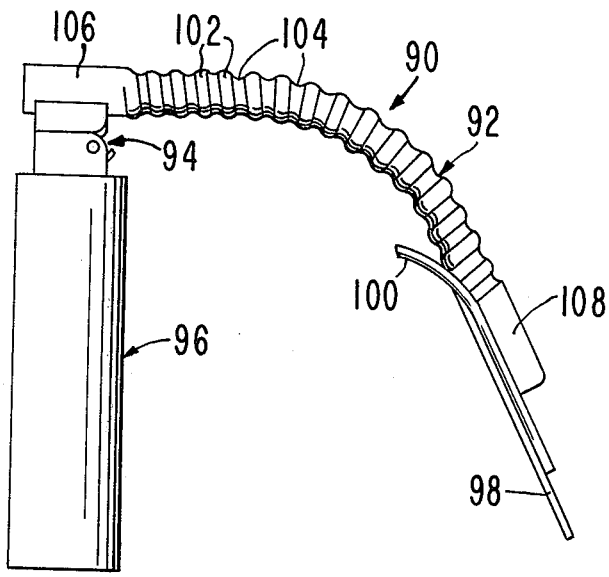
FIG. 14 is a view similar to FIG. 13 but showing another type of flexible blade.

FIG. 14 shows a laryngoscope 90 having a tubular, slotted blade 92 pivotally coupled by pivot means 94 to a handle 96. Blade 92 has a pad 98 and a fiber optic viewing member 100 associated with it, member 100 being provided with or without a self-contained light source. Laryngoscope 90 is essentially the same in function and purpose as laryngoscope 10 and laryngoscope 80 except that blade 92 is capable of being shaped or flexed to permit it to assume any one of a number of different operative positions relative to handle 96. To this end, blade 92 is made of a suitable metal tubing having a slot 93 along its length and comprised of a number of enlarged, ring-like parts 102 with each pair of adjacent parts 102 being separated by a flexible thin-walled link 104 integral with parts 102. The upper end portion 106 and the lower end portion 108 of blade 92 are cylindrical. These end portions are not required to be flexed; thus, they need not be made like the middle part of blade 92. Laryngoscope 90 is used in the same manner as laryngoscope 80.

Figure 15:
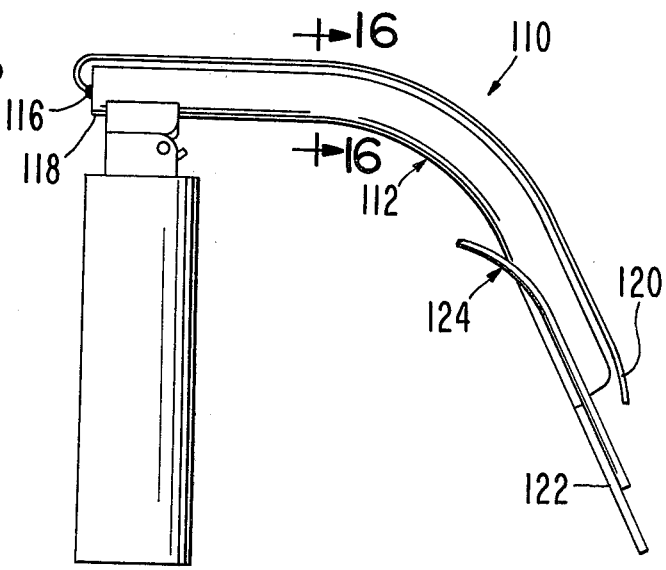
FIG. 15 is a view similar to FIGS. 1, 6 and 9 but illustrating another embodiment of the laryngoscope of the present invention.
Figure 16:
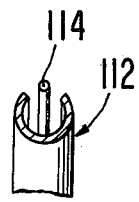
FIG. 16 is a cross-sectional view taken along line 16—16 of FIG. 15.
Figure 16A:
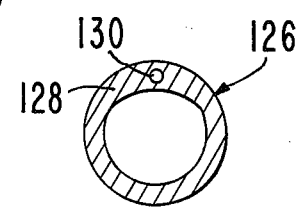
FIG. 16a is a cross-sectional view of an improved endotracheal tube suitable for use with the laryngoscope of FIGS. 15 and 16.

In the laryngoscopes set forth above, the blades of the laryngoscopes have been described as being tubular to guide an endotracheal tube or to guide medical instruments into the throat area of the patient. FIGS. 15 and 16 show a laryngoscope 110 having a blade 112 which is generally crescent shaped in cross section as is shown in FIG. 16 to present an open lower margin. By virtue of this open cross-section, the blade could not adequately guide a tube into the throat of a patient. For guidance purposes, the blade has a guide wire 114 near the top margin of the blade. Wire 114 has an upper end 116 which is secured in any suitable manner to the upper end 118 of blade 112. The wire extends longitudinally of the blade along and slightly above the bottom margin and terminates at the lower end 120 of the blade near pad 122 which is the same in size and purpose as pad 28 of laryngoscope 110 (FIG. 1). A fiber optic viewing member 124 and a light source (not shown) are also associated with blade 112 for the same purpose as light source 32 and member 38 of laryngoscope 10.

In using laryngoscope 110, the endotracheal tube (not shown) to be inserted into the larynx of the patient is first moved onto wire 114 from the free end of the wire and held by the wire on blade 112 by virtue of the wire's being in the lumen of the endotracheal tube. Then the blade is inserted into the throat of a patient and the blade elevates the epiglottis. The wire guide then positions the endotracheal tube so that it can be advanced into the larynx and trachea by advancing the tube longitudinally along the wire guide. When this has occured, the endotracheal tube is held in place as blade 112 is removed from the throat. The wire thus serves as a holder for the endotracheal tube and also serves as a guide for removal of the blade from the throat area after insertion of the tube thereinto.

In an alternate embodiment, the endotracheal tube 126 can have a thickened side wall portion 128 provided with a longitudinal, passage 130 therethrough which receives wire 114. Tube 126 is moved onto the wire by inserting the wire into passage 130 before blade 112 is inserted into the throat of the patient. The tube is then moved off of the wire into the larynx after the larynx is viewed and the wire is properly positioned. The tube is held in position as the blade is removed.

FIG. 17 shows a laryngoscope 120 which has an improved mechanical and electrical connection between the metallic tubular blade 122 thereof and a tubular handle 126 having a battery therein. The blade is mounted by being embraced by a short tubular extension 127 on handle 126 and the handle has a metallic spring contact 130 comprised of two spring members adjacent to each other, the spring members being shaped like a pair of cymbals. A ball bearing 132 which is electrically conductive is held in place against a seat 134 on blade 122 by spring 130, the opposite end of the spring engaging the electrical terminal 136 of the battery. A boss 138 on blade 122 has seat 134 and makes electrical contact between the blade and, the terminal 136 of battery 124 when the blade is snapped into its operative position shown in FIG. 17. A side slot 142 for viewing purposes is provided in the blade. FIG. 17a shows a similar blade and handle combination except that the side slot 142 is located at a different circumferential position from that of the slot of FIG. 17.

FIG. 18 shows another view similar to FIG. 17 but showing a second way in which a mechanical connection and electrical contact can be made between the blade and the handle. To this end, a spring 150 having a ball bearing 152 received in a seat in a boss 154 is mechanically coupled to a metallic, tubular blade 156. Spring 150 is carried by handle 157 which has a tubular part 161 embracing blade 156. The central terminal of a battery 160 in the handle is connected by a conducting lead 164 to a boss 166 spaced from boss 154 on blade 156. The blade has a side slot 168 for viewing purposes. FIG. 18a shows slot 168 at a different circumferential location from that of the slot shown in FIG. 18.

In order to ensure sterility, disposable plastic inner liners for the laryngoscope blade may be needed. These will be thin, flexible and basically will conform to the inner configuration of the blade. That is to say they will have a terminal pad, posterior groove and slots or grooves which will allow optic guides or light sources to go through, if necessary. Under these conditions the endotracheal tube which itself is sterile will only touch a steril surface of the laryngoscope blade.

In order that one laryngoscope blade may be used for several different sizes of endotracheal tubes, small shims may be necessary which will close down the width of the posterior groove in the laryngoscope blade. Thus, tubes which are smaller in diameter than the groove in the laryngoscope blade itself may be retained by the shims which will be attached to the edges of the laryngoscope blade along its grooved margin.

I claim:

1. In a laryngoscope of the type having a handle: a generally self-sustaining blade having a first end, a second end, and means at the first end thereof for attaching the same to the handle, the blade being curved at a portion thereof intermediate the ends, the blade adapted to be inserted into the throat of a patient and being tubular along its length to present a guide to permit a flexible, elongated member to be directed along and through the blade and into the throat, said blade having a slot therein at a location permitting a view of the throat through and along a portion of the blade as the blade is initially inserted in the throat, said slot being sufficiently narrow to retain said flexible member within the tubular blade as said member is guided therethrough from said first end to said second end; means coupled to the blade for presenting a light source near the second end thereof; an elongated fiber optic viewing member having a first end face near said second end and extending at least partially along the blade toward said first end thereof, said viewing member having a second end face for viewing light striking said first end face of the member.

2. In apparatus as set forth in claim 1, wherein the slots extends along substantially the entire length of the blade.

3. An apparatus according to claim 2 wherein said slot is narrower than the cross-sectional dimension of said flexible member when the latter is in a relaxed condition but sufficiently wide to allow said member to be passed therethrough when the member is squeezed or otherwise deformed in a way which reduces its cross-sectional dimension, whereby to separate said blade from said member after the latter has been inserted through the blade.

4. In apparatus as set forth in claim 1, wherein the slot extends only partially along said blade including said curved portion and said second end.

5. In apparatus as set forth in claim 1, wherein the blade has a pair of diametrically opposed side margins, the slot being at a location between the side margins.

6. In apparatus as set forth in claim 1, wherein the second end of the blade has a flat pad thereon, the light source and the end face of the viewing member being on one side of the pad.

7. In apparatus as set forth in claim 1, wherein the blade has a circular cross-section throughout a major portion of its length so that the blade can be used as an operating laryngoscope to permit the insertion of surgical tools into the into the throat through the blade itself.

8. In apparatus as set forth in claim 1, wherein the blade has a channel element at one side thereof near the second end, said viewing member being removably inserted in the channel element.

9. In apparatus as set forth in claim 1, wherein the viewing member has an outer, flexible sheath, and including means for securing the sheath to the blade so that the sheath extends along the blade.

10. In apparatus as set forth in claim 9, wherein the viewing member has a length greater than the blade to present a projecting portion near said first end of the blade, the projecting portion being flexible to permit the viewing member to extend away from said first end of the blade and then to be moved into position extending generally parallel to the blade.

11. In apparatus as set forth in claim 1, wherein the blade is of a material which can be flexed so that the curvature of the blade can be adjusted in shape to fit different throat configurations.

12. In apparatus as set forth in claim 11, wherein the blade is formed from a thermoplastic material.

13. In apparatus as set forth in claim 11, wherein the blade is formed from a metallic, bellows-like material.

14. In a laryngoscope of the type having a handle; a blade having a first end, a second end, and means at said first end thereof for attaching the same to the handle, the blade being curved at a portion thereof intermediate the ends, the blade adapted to be inserted into the throat of a patient and being tubular along its length to present a guide to permit an elongated, flexible member to be directed along and through the blade and into the throat, said blade having a slot therein at a location permitting a view of the throat through and along a portion of the blade as the blade is initially inserted in the throat, said slot being sufficiently narrow to retain said flexible member within the tubular blade as said member is guided therethrough from said first end to said second end, the blade being of a material which is relatively self-sustaining and capable of being flexed, so that the curvature of the blade can be adjusted in shape to fit different throat configurations.

15. In apparatus as set forth in claim 14, wherein the slot extends along substantially the entire length of the blade.

16. In apparatus as set forth in claim 15, wherein the blade has a pair of opposed side margins, the slot being between the side margins.

17. An apparatus according to claim 15 wherein said slot is narrower than the cross-sectional dimension of said flexible member when the latter is in a relaxed condition but sufficiently wide to allow said member to be passed therethrough when the member is squeezed or otherwise deformed in a way which reduces its cross-sectional dimension, whereby to separate said blade from said member after the latter has been inserted through the blade.

18. In apparatus as set forth in claim 14, wherein the slot extends only partially along said blade including said curved portion and said second end.

19. In apparatus as set forth in claim 14, wherein the second end of the blade has a flat pad thereon.

20. In apparatus as set forth in claim 14, wherein the blade has a circular cross-section throughout a major portion of its length so that the blade can be used as an operating laryngoscope to permit the insertion of surgical tools into the throat through the blade itself.

21. In apparatus as set forth in claim 14, wherein the blade is formed from a thermoplastic material.

22. In apparatus as set forth in claim 14, wherein the blade is formed from a metallic, bellows-like material.

23. A blade for use as part of a laryngoscope which also includes a handle, said blade comprising: a generally rigid body in the form of an elongated tubular member having opened front and back ends and defining a curved path along an intermediate section of the member between said ends, said member being adapted for insertion through the throat of a patient and into the pharynx so as to provide an inner guideway between said opened ends for receiving a flexible endotracheal tube or other similarly shaped flexible item from said back end and for guiding said tube or item into the patient's larynx; means carried by said tubular member adjacent its back end for connecting said member with said laryngoscope handle; and a slot extending at least the length of and opening into the intermediate section of said tubular member so as to provide an unobstructed view of portions of the throat and ultimately the larynx through the slot as the tubular member is inserted into the throat and so long as the intermediate section of said tubular member is internally empty, said slot being sufficiently narrow widthwise to retain said flexible tube or other item within said guideway as the tube or item is caused to move therethrough along said curved path from said back end to said front end.

24. An apparatus according to claim 23 wherein said slot extends the entire length of said tubular member from said back end to said front end, said slot being narrower than the cross-sectional dimension of said flexible endotracheal tube or similar item when the latter is in a relaxed condition but sufficiently wide to allow said tube or item to be passed therethrough when the tube or item is squeezed or otherwise deformed in a way which reduces its cross-sectional dimension, whereby to be able to separate the blade from said tube or item after the latter is inserted through the tubular member of the blade.

25. An apparatus according to claim 24 wherein said slot is located along the outside of said curved path defined by said tubular member.

26. An apparatus according to claim 23 wherein said generally rigid body is relatively self-sustaining but can be flexed so that it can be adjusted in shape in order to vary said curved path in order to fit different throat configurations.

27. A laryngoscope, comprising: a handle; a blade including a generally rigid body in the form of an elongated tubular member having opened front and back ends and defining a curved path along an intermediate section of the member between said ends, said member being adapted for insertion into the throat of a patient so as to provide an inner guideway between said opened ends for receiving a flexible endotracheal tube or other similarly shaped flexible item from said back end, whereby to guide said tube or other item into and along the patient's throat and ultimately into the patient's larynx and trachea, said blade also including a slot extending the entire length of and opening into said tubular member from said back end to said front end so as to provide an unobstructed view of portions of the throat and ultimately the larynx through the slot as the tubular member is inserted into the throat and so long as the tubular member is internally empty, said slot being narrower than the cross-sectional dimension of said flexible tube or other item when the latter is in a relaxed condition so as to thereby retain said tube or other item within said guideway as the tube or item is caused to move therethrough along said curved path from said back end to said front end, said slot being sufficiently wide to allow said tube or other item to be passed therethrough when said tube or item is squeezed or otherwise deformed in a way which reduces its cross-sectional dimension, whereby to separate said blade from said tube or item after the latter has been inserted into the blade; and means for disengagably connecting the back end of said blade to one end of said handle.

28. A laryngoscope according to claim 27 including means cooperating with said blade body for providing light at the front end of the latter whereby to illuminate a given area adjacent said front end and means also cooperating with said blade body for viewing said illuminated area from a location adjacent the back end of said blade body, even after said blade body has been inserted into the patient's throat.

29. An assembly especially suitable for use in carrying out an anesthesia procedure on a patient, said assembly comprising: a flexible endotracheal tube having opposite front and back ends and a predetermined maximum outer cross-section along its length; and a laryngoscope for placing a front end segment of said tube within the throat of a patient and ultimately into the patient's larynx and trachea, said laryngoscope including a handle and a blade disengagably connected with said handle, said blade including a generally rigid body in the form of an elongated tubular member having opened front and back ends and defining a curved path along an intermediate section between its front and back ends, said member being adapted for insertion into the patient's throat so as to provide an inner guideway between said opened ends for receiving said flexible endotracheal tube from said back end whereby to guide said front end segment of said tube into said patient's throat, said blade also including a slot extending the entire length of and opening into said tubular member so as to provide an unobstructed view of portions of the throat and ultimately the larynx through the slot as the tubular member is inserted into the throat and so long as the intermediate section of said tubular member is internally empty, said slot being narrower than the outermost cross-section of said tube when the latter is in a relaxed condition whereby to retain the tube within the guideway as the tube is caused to move therethrough from said back end to said front end, said tube being sufficiently wide to allow said tube to be passed therethrough when the tube is squeezed or otherwise deformed in a way which reduces its outer cross-section, whereby to separate said blade from said tube after the latter has been inserted through the blade and into the throat of the patient.

30. A method of placing the front end segment of a flexible endotracheal tube or like item into the throat and ultimately the larynx and trachea of a patient, said method comprising the steps of: providing said tube or similar item; providing a laryngoscope which includes a handle and a blade connected with said handle, said blade including a generally rigid body in the form of an elongated tubular member having opened front and back ends and defining a curved path along intermediate section of the member between said ends and a slot extending at least the length of and opening into the intermediate section of said tubular member so as to provide an unobstructed view of portions of the throat and ultimately the larynx through the slot as the tubular member is inserted into the throat and so long as the intermediate section of said tubular member is internally empty, said slot being sufficiently narrow to retain said flexible tube or other item within said guideway as the tube or item is caused to move therethrough along said curved path from said back end to said front end; with the intermediate section of said tubular member internally empty, inserting a section thereof including its front end into said patient's throat while looking through said slot from said one side to said other side for viewing areas of the throat made visually accessible by said slot; after said blade has been placed in the desired position within the patient's throat and ultimately the larynx and trachea, inserting said front end segment of said tube or other item through said tubular member from its back end, whereby the flexible member is caused to conform to the curved shape of said member.

31. A method according to claim 30 wherein said slot extends the entire length of said tubular member, said slot being narrower than the cross-sectional dimension of said flexible tube or other item when the latter is in a relaxed condition but sufficiently wide to allow said tube or other item to be passed through said tubular member when said tube or other item is squeezed or otherwise deformed in a way which reduces its cross-sectional dimension, said method including the step of removing said laryngoscope blade from the patient's throat while leaving said tube or other item in place after the latter has been so positioned, said blade being removed by squeezing or otherwise deforming said tube or other item sufficient to pass it through said slot.

32. A method according to claim 30 including the steps of providing light at the front end of said tubular member as the latter is inserted into the patient's throat so as to illuminate the surrounding area and viewing said area from outside the throat using fiber optic means to do so.

* * * * *